(12) United States Patent
Locklear (10) Patent No.: US 10,032,004 B1
(45) Date of Patent: Jul. 24, 2018

(54) METHOD AND SYSTEM TO IMPLEMENT MEDICAL INFORMATION TRACKING SYSTEM AND MEDICATION DISPENSER

(71) Applicant: Stuart Renwick Locklear, Pembroke, NC (US)

(72) Inventor: Stuart Renwick Locklear, Pembroke, NC (US)

( * ) Notice: Subject to any disclaimer, the term of this patent is extended or adjusted under 35 U.S.C. 154(b) by 571 days.

(21) Appl. No.: 14/575,880

(22) Filed: Dec. 18, 2014

Related U.S. Application Data (60) Provisional application No. 61/917,853, filed on Dec. 18, 2013.

(51) Int. Cl.
*G06F 19/00* (2018.01)

(52) U.S. Cl.
CPC ............... *G06F 19/3462* (2013.01)

(58) Field of Classification Search
CPC .... G06Q 10/00; G06Q 50/00; G06F 19/3462; G16H 20/13; G16H 20/60; G16H 20/70; G16H 20/90
See application file for complete search history.

(56) References Cited

U.S. PATENT DOCUMENTS

| | | | |
|---|---|---|---|
| 2002/0147526 A1* | 10/2002 | Siegel | A61J 7/0481 700/237 |
| 2003/0006242 A1* | 1/2003 | McKinney, Jr. | A61J 7/0481 221/76 |
| 2013/0092700 A1* | 4/2013 | Braunstein | G07F 9/006 221/13 |

* cited by examiner

*Primary Examiner* — Linh Giang Le
(74) *Attorney, Agent, or Firm* — Vista IP Law Group, LLP (57) ABSTRACT

Disclosed is a cloud-based resource and information tracking system for medical patients and healthcare providers. The cloud-based software system integrates all or many sources of patient medical and health information, updates the information in near real-time, and makes the data available to member(s) of the patient's healthcare team securely.

13 Claims, 9 Drawing Sheets

METHOD AND SYSTEM TO IMPLEMENT MEDICAL INFORMATION TRACKING SYSTEM AND MEDICATION DISPENSER

CROSS REFERENCE TO RELATED APPLICATIONS

The present application claims the benefit of U.S. Provisional Application No. 61/917,853, filed on Dec. 18, 2013, which is hereby incorporated by reference in its entirety

BACKGROUND

The healthcare IT (information technology) marketplace is currently dominated by IT systems that are relatively inefficient and lack state-of-the-art technology. The lack of efficient, sophisticated IT systems and services that address the rapid changes in the healthcare industry is a serious impediment to reducing service costs and improving the quality of healthcare.

These problems are further exacerbated by modern governmental policies and regulations, where governments continue to reduce and limit compensation for critical services and patients. Governments now also expect healthcare providers to offer ongoing preventive care, especially for chronic conditions, even when the patient is not actively under a physician's care. While many single-point solutions exist, their isolation from other systems and limited scope reduces their effectiveness in providing satisfactory solutions to critical problems. Additionally, since no single healthcare IT service provider offers a cost effective, comprehensive solution that addresses all the needs of healthcare providers and patients, each caregiver organization must piece together a "custom" solution on their own.

Consequently, there is a significant need for a universally accessible, fully integrated, intelligent solution that helps improve the quality of care while improving efficiency.

SUMMARY

Embodiments of the present invention provide a cloud-based resource and information tracking services for medical patients and healthcare providers and develop a hardware device that solves significant healthcare problems, including the problems described above.

Other additional objects, features, and advantages of the invention are described in the detailed description, figures, and claims.

DETAILED DESCRIPTION

Integration Platform

In some embodiments, the invention pertains to a cloud-based software system that integrates all/many sources of patient medical and health information, updates the information in near real-time, and makes the data available to each member of the patient's healthcare team securely, anytime and anywhere Internet access is available.

Figure 1:
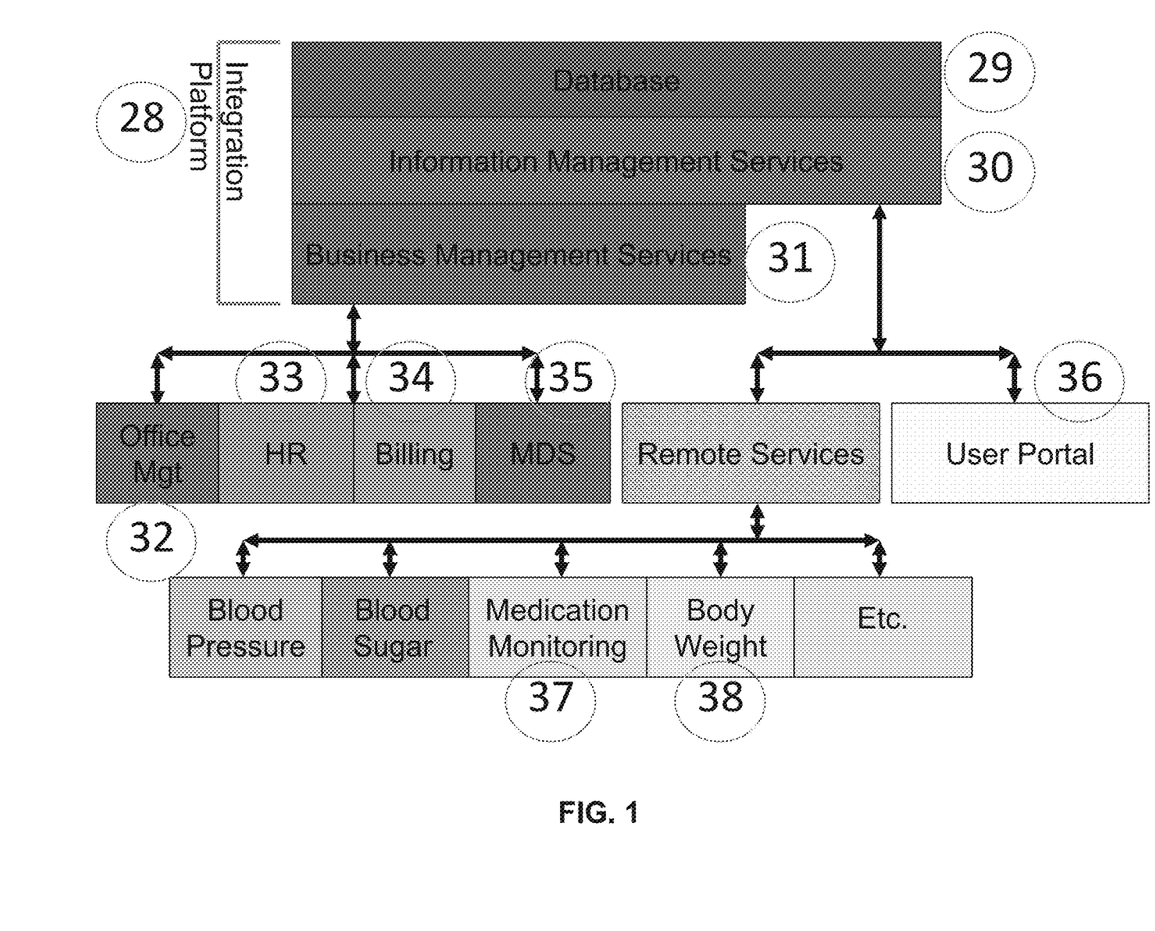
FIG. 1 provides an illustration of an example architecture that can be used in some embodiments of the invention to implement the integration platform.

FIG. 1 provides an illustration of an example architecture that can be used in some embodiments of the invention to implement an integration platform 28. The system 28 integrates information from doctors' offices, hospitals, test labs, state organizations, remote and mobile devices and other sources. To accomplish this goal, the inventive approach is flexible enough to handle differences in information sources for different types of users and different user requirements.

A high-performance database 29 that serves as a data repository is the basis for the software product and services. Additional logic modules provide information 30 and business management services 31. Together, the database 29 and the information 30 and business management logic modules 31 comprise the integration platform 28 that manages data and information collected and/or generated by the system. The integration platform's modular design allows the addition of new data sources without a disruption to an existing user's service and allows each user's experience to be customized to their particular needs.

The design also allows all of a patient's health and medical information to be available during a hospital stay or doctor's visit. The latest information will then be immediately available to nursing home personnel, a homecare professional, an assisted-living aide or any another authorized HCP. The patient's medical history will be available 24 hours a day, 365 days per year anywhere in the world that has Internet access.

Various business modules can be deployed in the integration platform. In the illustrative example, four business modules are included, including for example: office management (OMM) 32, human resources management (HRM) 33, minimal data set module (MDS) and customer billing (CBM) 34.

The office management module 32 provides employee and customer scheduling services. Patients can make appointments online and the system will confirm by phone, e-mail or text message the patient's intent to visit the doctor at the designated time. The system will also provide resource management for exam rooms, test devices, and other office resources. The system will calculate and display performance information such as the number of patients treated in a specific time period, the amount of time spent with each patient, the number of prescriptions written in a specific time period, etc. The system can manage multiple locations for the same organization and compare the performance of multiple locations.

The human resource module 33 manages all data and information related to employees. A healthcare provider (HCP) can manage their personal and certification information with the HRM. The HCP can upload copies of required certification information such as a copy of a driver's license, fingerprints, ongoing education course completion certificates, criminal background checks, etc. The user may set a date to be notified by phone, e-mail or text message of the impending expiration of critical information. The system will come with a set template for certification information but the user may add additional items to the list to create a customized version of their professional experience.

The HRM 33 will also allow HCPs to automatically transfer HR data between organizations. All files and other information will be transferred from the HCPs personal file to the potential employer's online application system. A notice will be sent to both parties if any information is missing or if the application is incomplete.

The HRM 33 will also monitor the hiring process. Once an employment application is complete, the responsible party will be notified that the application is ready for review. When the application is reviewed, the reviewer can accept the application and schedule an interview. The interviewer can notify applicant of the interview's particulars, date, time, place, etc., with assistance of the system. If the applicant is rejected, the reviewer can notify the applicant using system communications. If the applicant successfully passes the interview, the interviewer may automatically transfer the applicant's information into the employee category.

The HRM 33 manages the employee's experience and performance information, as well as availability status, vacation time, performance history, etc.

The customer-billing module 34 tracks services provided to a patient by ICD codes and automatically files the invoice to Medicare or pushes the billing information into the organization's financial system. The treatment tracking functionality will automatically prioritize treatments per the number of occurrences in particular office. Consequently, each HCP office will have a customized tracking service sheet instead of a standard list that may not be suitable for that particular office.

Finally, the MDS 35 module digitizes the standard MDS form, allows the healthcare team to collectively review the patient's treatment protocol, manages any changes to the patient's treatment, tracks the patient's progress, and automatically calculates the patient's score. Once the information has been approved by all of the healthcare team members, the request for payment can be submitted directly to provider/payer/Medicare.

The user portal 36 integrates and displays the information gathered about the patient in one place and in an intelligent fashion for easy reference. The portal information will provide an up-to-date snapshot of the patient's condition and provide information to make better treatment decisions. The portal is customizable for each patient and user.

One advantage provided by the system is the integration of remotely generated information that is not currently available to a patient's healthcare team. Some information is currently reported but many times is simply written down and forgotten or not displayed in a useful manner to the HCP so it is ignored. Remote data collection is especially helpful in treating chronic diseases because the patient needs constant monitoring. This amount of attention is difficult and expensive when done by a caregiver but the situation is ideally suited for electronic monitoring and feedback.

Figure 2:
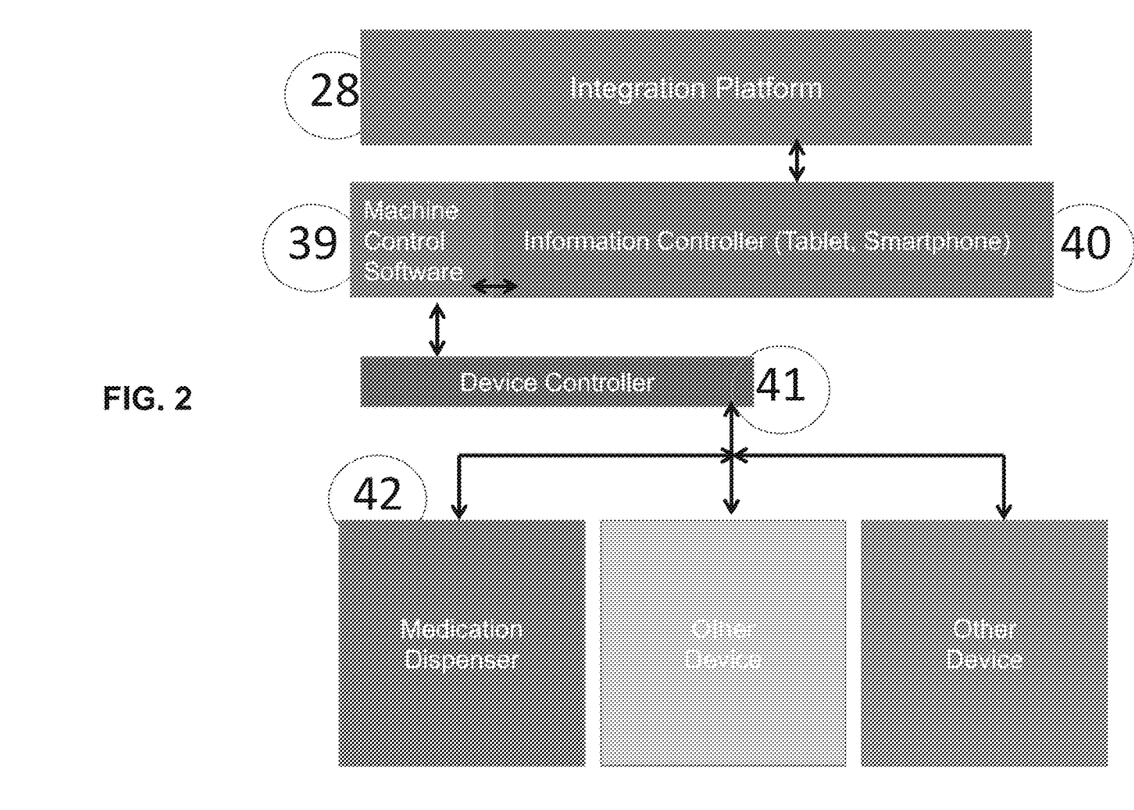
FIG. 2 is an illustration of the integration of the integration platform, remote dispenser control software, the dispenser controller and the dispenser.

For example, as shown in the architecture of FIG. 2, the system can be implemented to perform medication adherence 37 and body weight monitoring 38. In both cases, system hardware is employed to monitor a patient's weight and the complete medication cycle.

In these example implementations, the system 37 tracks a prescription from the time it is prescribed, when the prescription is filled, when the patient picks up the prescription, when the medication is loaded in the special dispenser. Once the medication is loaded into the dispenser 42, the system automatically delivers the mediation into a container and notifies the patient that it is time to take the medicine. Once the container is removed and replaced, the system will automatically update the status of the medication from dispensed to taken.

An intelligent device 40 such as a smartphone or tablet operates a device controller 41 to control the medication dispenser 42. The dispenser 42 and remote service controller are connected by a wired-USB connection. The controller is updated by the integration platform with the latest medication regimen when any changes occur to the patient's medication protocol. The dispenser 42 can hold more than a one-month supply of any pill-form medication. The user may dispense medication by manually operating the dispenser so medication may be taken at a different location than where the dispenser is located.

A scale 38 connected to the remote service controller by a wired-USB connection will measure body weight and input the results into the system. The patient's weight history can be displayed in the user portal for future reference.

Illustrative Embodiment

This section will now describe an illustrative embodiment of the invention that implements a medication dispenser. The following describes FIGS. 2-9, which provide detailed schematics of the components of a dispenser system according to some embodiments of the invention.

In the example system, the medication dispenser will consist of "x" number of base unit module(s) that hold one type of pill-form medication. The base unit module is designed to limit the amount of materials and cost of the dispenser.

Communications between the dispenser 42 and information system controller 41 can be handled over cabling, e.g., USB cabling. Alternatively, communications can be implemented using wireless communications hardware.

Medication is handled only in single doses, i.e., one single pill, at all times. The standard medication dispenser 42 is configured with 12 base unit modules to manage 12 individual pill-form medications. The same medication may be held in multiple base unit modules 8. Each base unit module can hold up to 33 doses of an individual medication.

Medication will be manually loaded into a base unit module 8, where the base unit modules are easy to load. The base unit module design helps eliminate mistakes in loading medication. Preferably, only one base unit module can be open at a time in preparation for and during loading. An optional video system can record the loading of medication into the base module units.

If a base unit module 8 is opened at an unscheduled time, the dispenser's monitoring system will be triggered and a history of the activity will be recorded. Base unit modules will be sealed once they are loaded. The dispenser's software monitoring system will confirm that each base module is sealed. The dispenser's software monitoring system will confirm the number of pills in each base unit module.

Figure 9:
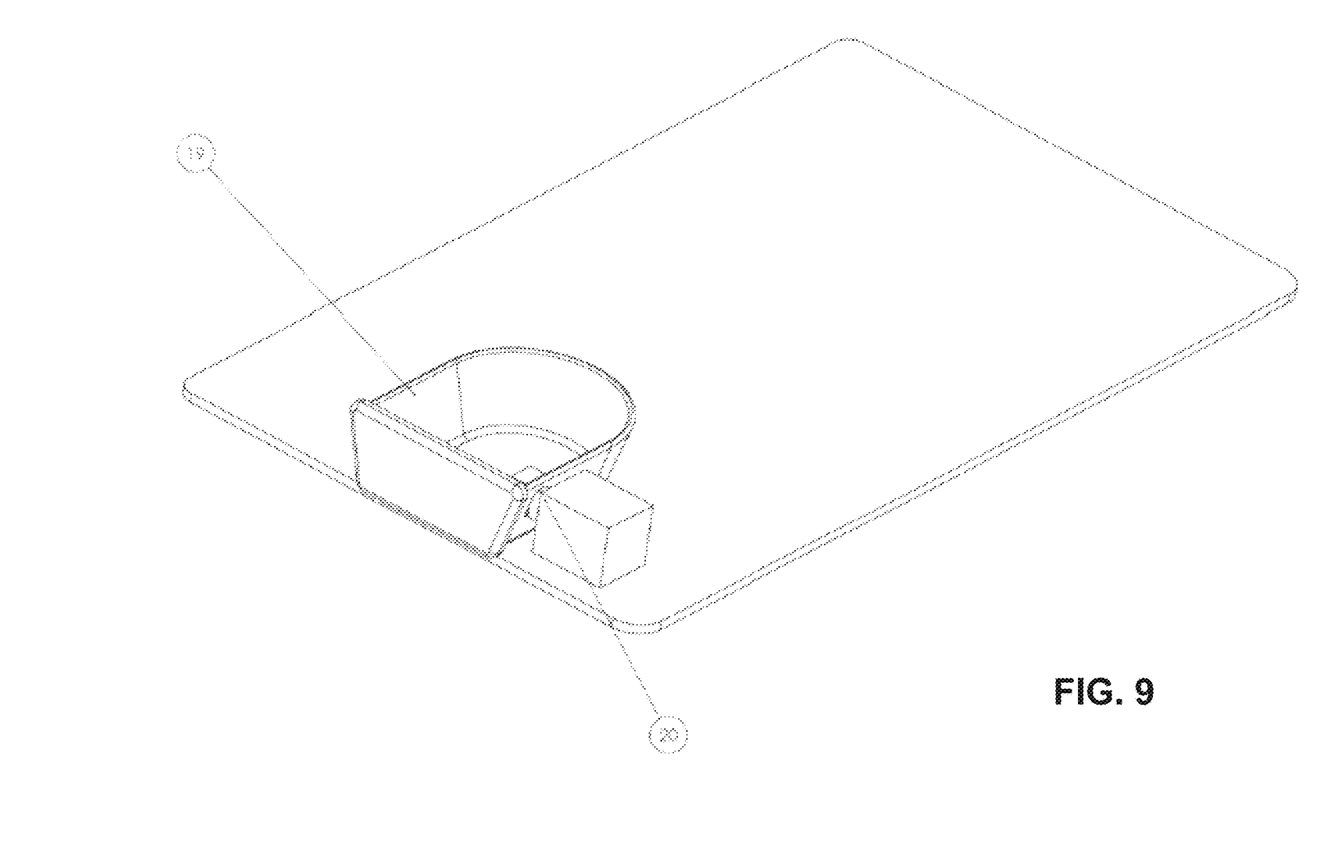
FIG. 9 shows details of the dispenser cup and software-controlled locking mechanism.

The medication dispenser will dispense the types of medication in the amount(s) and at the time(s) prescribed in the patient's medication protocol. Once the dispensed medication is confirmed to be correct amount, the medication will be deposited in a receptacle and ready for consumption. The dispenser's monitoring system will confirm the medication is taken within a pre-determined time by noting the removal and replacement of the medication receptacle 19. If the medication is not removed from the receptacle 19 within a predetermined time, a notice will be sent to pre-determined, concerned parties.

In terms of information technology, the system notifies healthcare team member(s) under various conditions. For example, a notification is provided if a medication is not on the approved medication list and/or provides notification that the dispenser may not operate properly. The system can notify healthcare team member(s) that the system is not functioning properly.

The system 39 is configured to compare dispensed medication-to-medication listed in treatment protocol. The system 39 confirms that the correct amount of medication is dispensed. The system 39 will notify healthcare team member(s) if an incorrect medication is dispensed. If the medication supply in a specific module is at or below the refill quantity, a notification will be sent to a concerned party. If a module 8 is empty, an urgent notification will be sent to several concerned parties. The system 39 will notify healthcare team member(s) if the incorrect type or incorrect amount of medication is dispensed.

After confirmation of the amount of medication the machine automatically deposits medication(s) into a cup. If the medication is not removed from the receptacle within a predetermined time, a notice will be sent to pre-determined, concerned parties. The system 39 can also notify health team member(s) at predetermined levels of medication for refill.

If a patient is requested to perform other activities before taking medication, the system 39 will prompt the patient to do these activities. Once the patient acknowledges these ancillary activities are complete, the system will dispense the patient's medication.

In some embodiment, the medication routine is remotely updatable. In addition, the system can manage multiple users.

Figure 7:
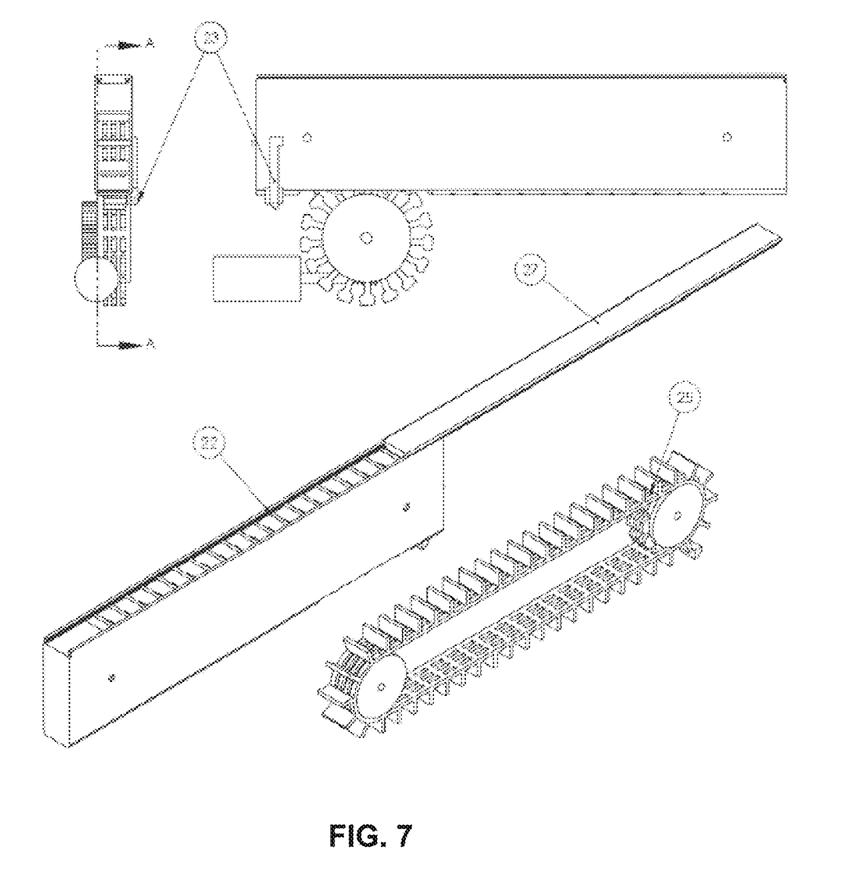
FIG. 7 is side view and component view of the module, paddle wheel, DC motor drive, module with module top and belt with paddle wheels.
Figure 8:
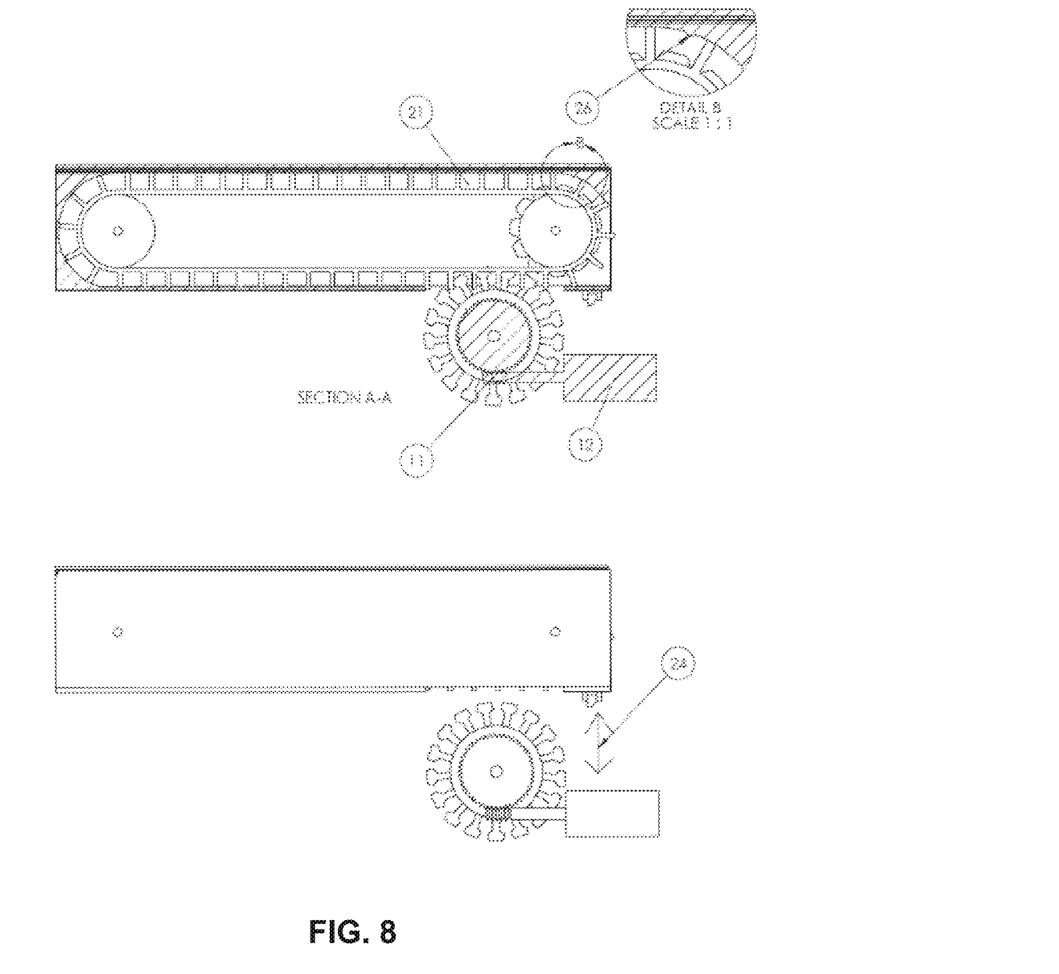
FIG. 8 is side view and component view of the module, paddle wheel, DC motor drive, belt with paddle wheels and details of the "bump" for releasing stuck pills.

A motor driven cogged belt 27 can be employed to implement the dispenser hardware. A separate belt compartment can be implemented for each pill. Each module 8 can be removed from the console unit with the motor drive left in place in the console. The "Paddle Wheel" drive engages the cogs in the belt allowing easy removal of the module from the console 1. The module can be loaded either while in the console or removed for remote loading and then replaced into the console. A separate DC drive motor 12 drives each console with a worm drive 1 between the motor shaft and the drive wheel, preventing "Back drive" while the module belt is parked.

The module 8 is designed such that pills can be loaded on both the front and back sides of the belt. A sliding access door 27 is on the front side of the module, but the belt can be rotated back to expose the empty cogged belt openings and load more pills, utilizing most of the belt length. In some embodiments, the belt can hold about 36 separate medications.

The use of a perforated belt 22 with pegs on the nose wheel provides positive ejection of the pill from contact with the belt.

Figure 5:
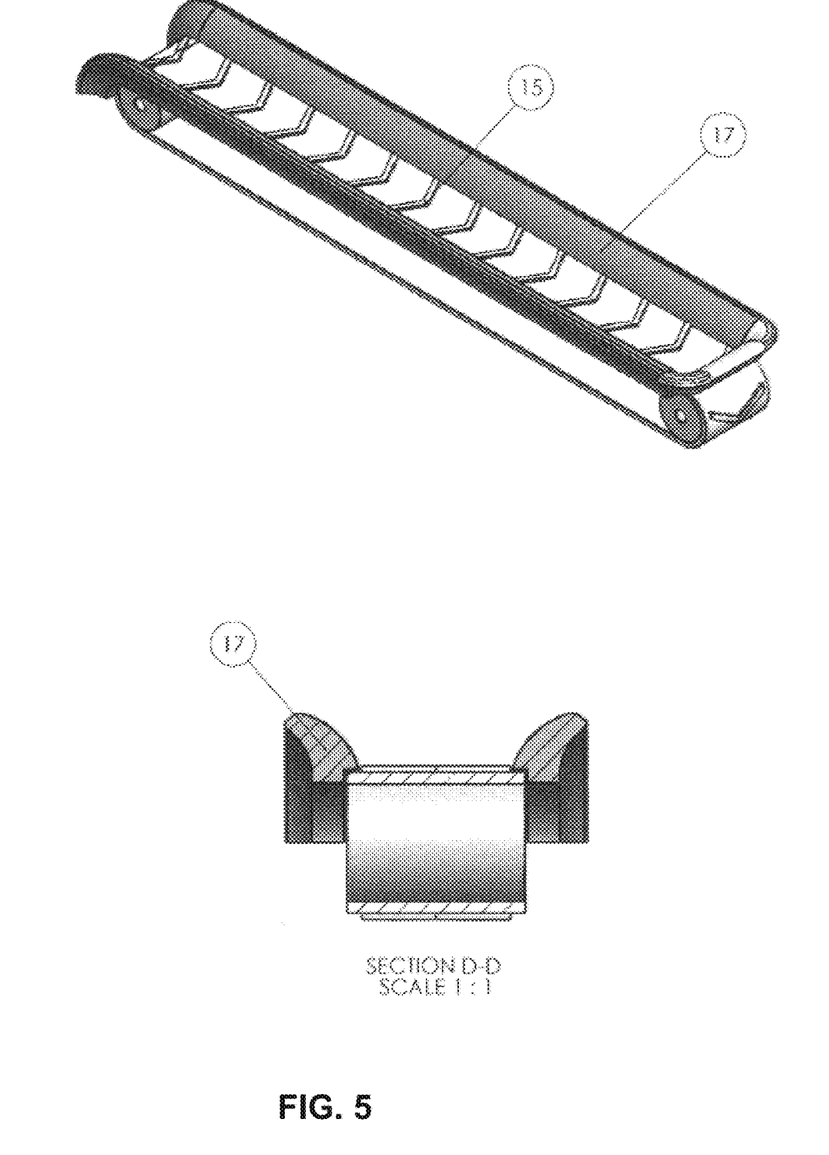
FIG. 5 is a side view and cutaway view of the transverse belt mechanism: belt, side rails and pulleys.
Figure 6:
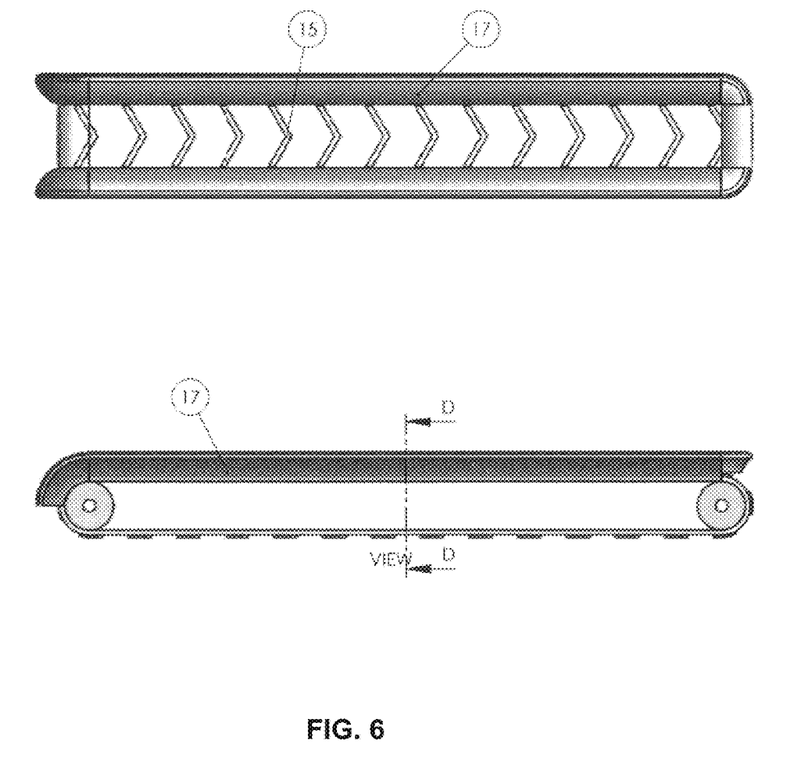
FIG. 6 is a top and side view of the transverse belt mechanism: belt, side rails and pulleys.

The cross feed belt 15 delivers the medications from each of the dispensing belts to the collection cup. This feature allows the use of a small collection cup 19 and a single pill delivery confirmation sensor 18 is used on the cross feed belt, eliminating the need for a separate confirmation sensor at each of the dispensing belts.

The pill collection cup 19 can be designed either from the front of the machine or from the side. The front location does require a longer draw to reach the cross feed belt exit point. Each feeder module has a sliding lid covering the pill locations in the belt cogs. The overall console has a hinged lid that covers all the feeder modules and locks down in place with an electro-mechanical locking system 6 that is software controlled and password protected.

The information/computer systems for this type of dispenser system have certain control features. For example, feedback confirmation is provided from sensors 9 to record essential events. Inventory levels of the dispensed medications are identified for comparison to the restocking requirements when the machine is to be refilled.

Translation is performed of the medication schedule into a "load map" showing where what medications are loaded into the machine.

In addition, information is provided to the machine control interface 39 to actuate the proper motors and mechanisms. A medication collection cup 19 presence and removal sensor is provided to interpret that the medication cup has been removed and replaced, inferring that the patient has taken the medications.

The overall system will have a battery backup power system allowing the system to operate multiple days on battery power if necessary. The recharging of the battery is accomplished through the console power supply while the unit is under AC power.

Console

Figure 3:
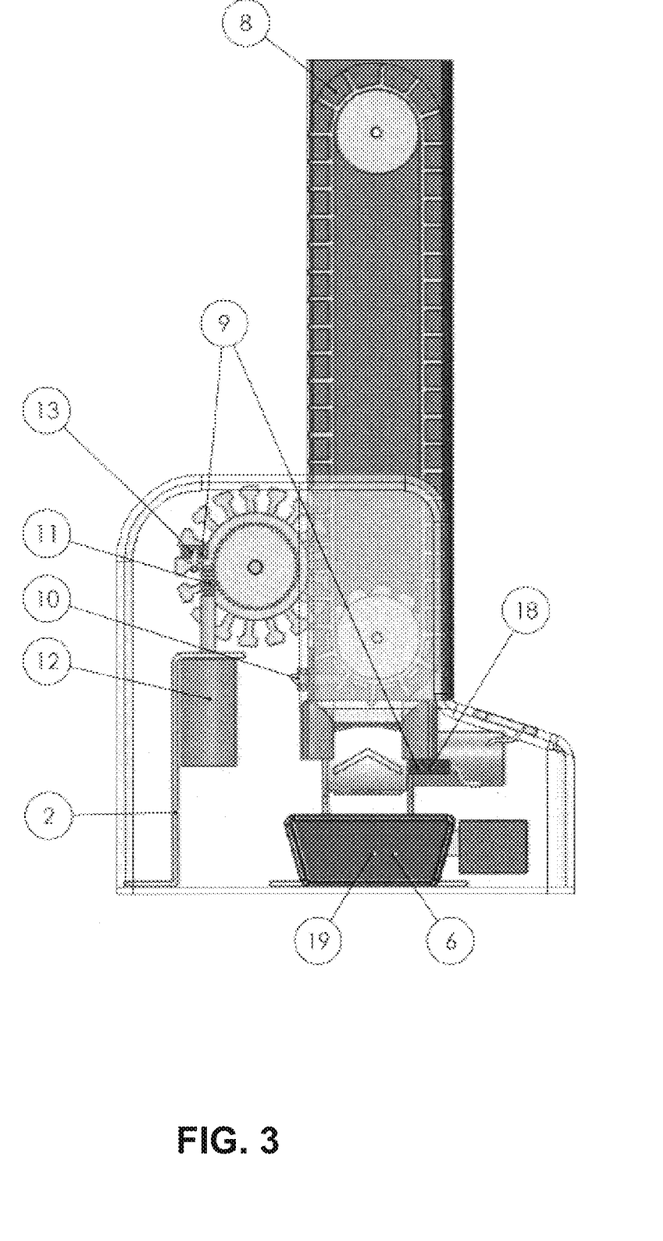
FIG. 3 is a side view of the console, modules, DC drive motor with worm drive, bracket for DC motor, transverse belt, dispenser cup, dispenser cup locking mechanisms, sensors and sensor mounts.
Figure 4:
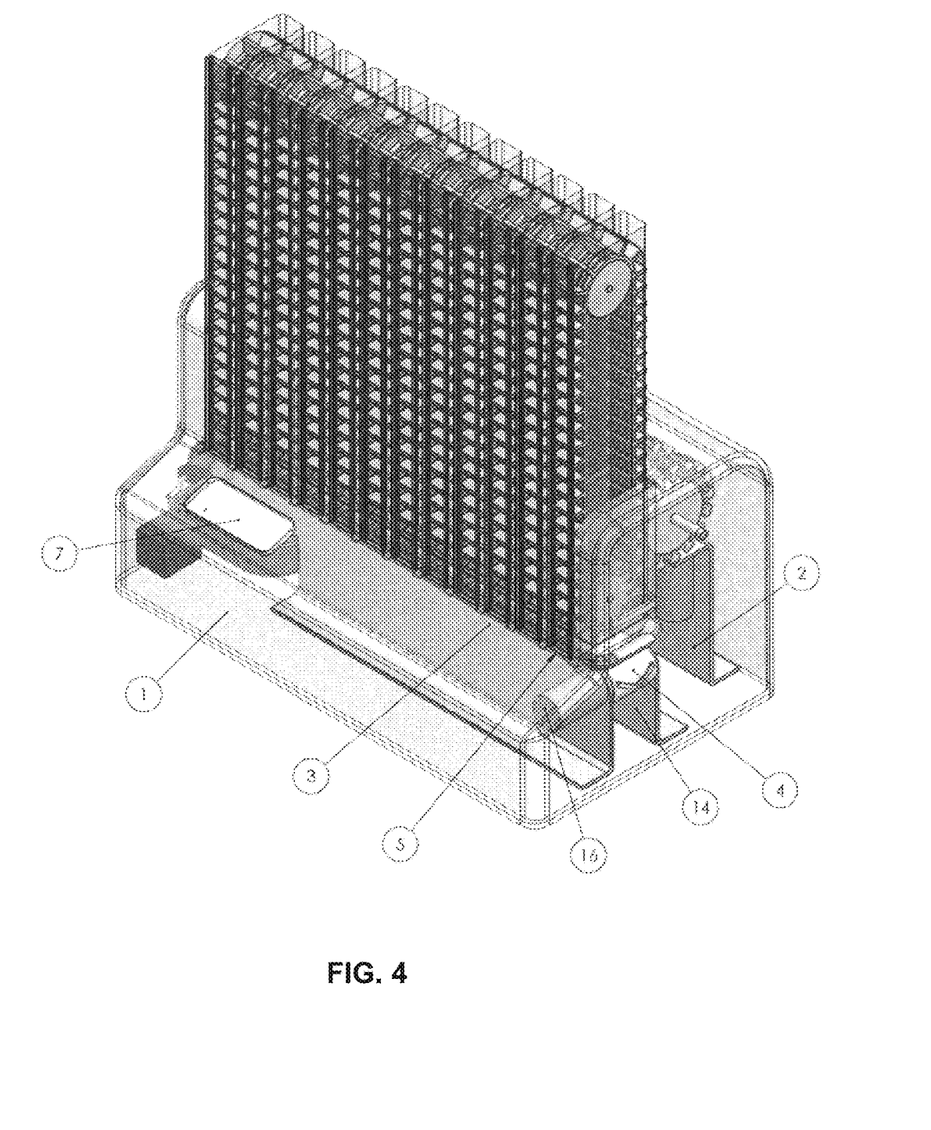
FIG. 4 is a side view of the console, modules, cross feed DC drive motor, bracket for DC motor, transverse belt, dispenser cup, dispenser cup locking mechanisms and LCD screen.

As shown in FIGS. 3-4, the console is comprised of a plastic case 1 which incorporates a support bracket 2 for the paddle wheel DC drive motor 12 with worm drive 11 attached and a support 3 for pill modules 8. The case 1 provides attachment mechanisms 14 for a cross feed belt 4 and cross feed belt DC drive motor 16. A locking mechanism 5 secures the modules from tampering. An LCD display 7 display the system status. The plastic module 8 seals the pill inventory from dirt. Mounting points 9 contained in the case 1 allow sensors to be mounted in the case. Locking mechanisms 10 allows manual locking and unlocking of the belt rotation, allowing for normal rotation of the belt. Sensors 13, 18 control movement of the belt and delivery of medication. The pill collection cup 19 is controlled by a software-controlled locking mechanism 6, 20 that secures the pill collection cup 19.

Paddle Wheel Drive

The worm drive 11 is a tubular extension with screw threads on the paddle wheel interface end and internal female threads on the DC motor face end and is connected to the DC drive motor 12. The DC drive motor 12 drives the paddle wheel drive wheel. The DC motor 12 will not have any integrated controls or sensors but will depend on feedback from the belt position sensor system to signal when one place increment has occurred. A resident sensor 13 will determine the movement of exactly one pill position. The DC drive motor 12 characteristics provide natural resistance to back driving. Pill modules 8 can be easily engaged and disengaged from the DC drive unit.

A sensor through beam transverses the entire width of the modules 8, which allows the monitoring of belt/paddle wheel movement from any module with only one sensor. The sensor beam utilizes the spacing between the individual paddle wheel teeth as the clear path for the sensor beam. As the wheel rotates, the rotating wheel blocks the beam until the next space between the teeth aligns with the beam, signaling that one belt increment has advanced on space.

Cross Feed Conveyor

The cross feed conveyor 14, 15 is supported by and contained in the dispenser housing and is driven by a DC motor coupled to a pulley on one end. The conveyor belt will have raised bumps to prevent the pill from rolling against the conveyor sidewalls. The side rails 17 are flared outward, providing a wider path to catch the pill as it is released from the module belt and falls onto the cross feed conveyor belt. The DC drive motor 12 will not have any integrated controls or sensors but depend on feedback from the pill arrival sensor system to signal when each pill has arrived at the collection cup and the cross feed belt can stop. A sensor 18 identifies that each pill has reached the collection cup. Only when each individual pill has arrived at the collection cup 19 will the operation sequence for the next pill begin. This sequence ensures that the complete and proper operations for each pill are performed and verified before operations for the next pill begin.

Pill Collection Cup

The pill collection cup 19 will have a custom shape to prevent the user from substituting other generic containers. A software-controlled latch 20 will prevent cup removal before the pill dispensing sequence is complete and when the dispenser is idle.

Pill Dispensing Module

The pill-dispensing module 8 is constructed of all molded plastic parts. The module belt design 21 provides for containment and separate of each individual pill. Each pill compartment is defined by the belt cleats, front and back, and by the module side rails on each side of the pill compartment. The pill-dispensing module is loadable while separated from the console 22. A belt rotation-locking feature prevents the belt from rotating when the module is separated from the console. This locking feature can be manually disengaged to rotate the belt during the loading sequence. The pill capacity of each module is achieved by loading both the front and back sides of the module belt. Loading involves initially loading a portion of the pill capacity on the front side and then rotating the belt to load the remaining portion on the backside of the belt.

Quick engagement with the paddle wheel drive is a key feature of the overall system 24. The feature allows the quick removal and replacement of the modules from the console. The ease of removal and replacement is achieved through the self-aligning engagement between the paddle wheel drive and the cleat features in the belt. As the module is inserted in the console, the belt rotation lock 23 is released first, which allows the belt to self-align with the drive paddle wheel. With the drive paddle wheel position maintained by the through beam sensor, the belt will self-align to the proper "parked" position. The perforated belt with ejector pins 25 is used to ensure that the pills don't stick to the base of the belt. The drive pins also service as ejector pins to lift the pills off the base of the belt as the pill arrives at the drop position at the bottom dead center.

A raised bump 26 on the module housing ensures that the pills do not remain stuck on the belt. As each cleat encounters the bump on the module housing, each divider is flexed, which creates a flicking action to break loose the sticking pills from the divider cleat.

Each module has its own lid 27 to prevent losing pills during loading and transport. The individual module lids are a sliding strip that uncovers the belt for loading and is returned to closed for transporting and reinstallation to the console. A locking feature prevents the belt from turning after the module is loaded and before it is returned to the console. As discussed in the module loading section, each module belt is locked from rotating when removed from the console to prevent inadvertent spillage of the pills during handling of the module. The locking feature can be manually disengaged to rotate the bell to another position while loading pills. Once manually released, the belt relocks until the module it returned to the console. A feature in the console releases the lock while the module is in the console, allowing normal rotation of the belt.

The materials used to manufacture the dispenser parts include at least some or all of the following: 1) Belt—molded urethane, 2) Housing—Injection molded plastic, 3) Belt pulleys—Injection molded plastic, 4) Sliding Lid—Extruded plastic and 5) Locking mechanism—Injection molded plastic.

Additional Features of the Illustrative System

The system is designed to be easy-to-use and maintenance and worry free. To achieve these goals, the device does not require any installation, maintenance or IT skills to setup or use. Device functionality is accessible on any Internet enabled device, such as, a PC, tablet or smartphone. Information generated by the patient is stored in a cloud-based system so backup of vital information is completed automatically and with a high level of security is assured. The system requires a password, passcode, fingerprint, facial scan or other secure information input to gain system access. The system is designed to allow easy integration with other systems to expand functionality and provide a seamless interconnection between all caregivers including physicians, pharmacist and patient. The system allows an administrator to manage several machines at multiple locations The system automatically checks for drug interactions when a prescription is initially written and when there is a change to a patient's medication regimen. If a negative drug interaction is identified, the concerned members of the healthcare team are notified immediately. System security ensures that only authorized healthcare providers make adjustments to a patient's medication regimen. The system automatically notifies the patient when to request a refill and also enables the patient to make medication refill requests electronically. The patient may change the location of the refill if so desired and the patient is notified of how many refills are remaining on the prescription. The system notes when a prescription is filled and can be configured to track the return of unused medications to a pharmacy or other disposal location.

The system will notify the healthcare provider which medication needs to be changed and indicate which module contains that particular medication. The system also tracks the number of doses loaded, the number doses remaining and prompts the patient or healthcare provider to confirm that the medication was taken. The system also records and saves a patient's medication history.

The Medication Dispenser Component

The device holds and manages up to 12 different types of pill-form or capsule medications and can hold up to 40 doses of each medication. A months supply of all 12 medications, 480 doses, can be loaded in approximately 20 minutes by a capable individual. After the medications are loaded, the device does not require patient or healthcare provider interaction to operate. The device does require user authorization to access or open the dispenser for loading or other adjustments. Access is controlled by a password, passcode, fingerprint and/or facial recognition and all access events are recorded and saved in a device history log that is available to each member of the healthcare team. The device will notify the patient and other healthcare team members that a medication needs to be changed and the device will not operate until the medication change is confirmed by an authorized use and is logged by the device. The device will signal that the device is unlocked and a module is open for loading. If more than one module is open, the dispenser will prompt the user to close one of the open modules. When medication is dispensed the device confirms that the medication has been deposited onto the transfer belt and also that the medication has been deposited into the dispenser cup. Optional features include a bar code reader for coded medications and a hardened case for increased security.

Therefore, what has been described is a cloud-based resource and information tracking system for medical patients and healthcare providers. The cloud-based software system integrates all or many sources of patient medical and health information, updates the information in near real-time, and makes the data available to member(s) of the patient's healthcare team securely.

In the foregoing specification, the invention has been described with reference to specific embodiments thereof. It will, however, be evident that various modifications and changes may be made thereto without departing from the broader spirit and scope of the invention. For example, the above-described process flows are described with reference to a particular ordering of process actions. However, the ordering of many of the described process actions may be changed without affecting the scope or operation of the invention. The specification and drawings are, accordingly, to be regarded in an illustrative rather than restrictive sense.

The invention claimed is:

1. A system, comprising:
a controller, wherein the controller comprises at least a tablet or smartphone that controls dispensing of medication; and
a medical dispenser that dispenses the medication when operated by the controller, wherein the medical dispenser comprises:
(a) a plurality of dispensing belts, a dispensing belt of the plurality of dispensing belts formed of a cogged belt that is engaged by a drive motor, wherein each of the plurality of dispensing belts corresponds to a separate medication for delivery, and the plurality of dispensing belts corresponds to a plurality of pill dispensing modules such that a first pill dispensing module having a first dispensing belt dispenses a first individual pill and a second pill dispensing module having a second dispensing belt dispenses a second individual pill; and
(b) a cross feed belt that delivers the medication from the plurality of dispensing belts to a collection cup;
wherein the plurality of dispensing belts is vertically oriented and the cross feed belt is horizontally oriented.

2. The system of claim 1, wherein the drive motor comprises a paddle wheel drive that engages cogs on the cogged belt.

3. The system of claim 2, wherein the paddle wheel drive comprises a worm drive having a tubular extension with screw threads on a paddle wheel interface end and internal female threads are located on a motor face end connected to a drive motor.

4. The system of claim 2, wherein the paddle wheel drive comprises a belt position sensor that signals when a one place increment has occurred for the dispensing belt.

5. The system of claim 1, wherein the plurality of dispensing belts comprises a perforated belt having pegs on a nose wheel.

6. The system of claim 1, further comprising an access door on a front side or a back side of the plurality of dispensing belts.

7. The system of claim 1, wherein the cross feed belt further comprises a pill delivery sensor conformation sensor.

8. The system of claim 5, wherein the pill delivery sensor conformation sensor provides delivery confirmation data for recordation.

9. The system of claim 6, wherein the inventory data is analyzed in conjunction with the delivery confirmation data to identify refilling requirements for the medical dispenser.

10. The system of claim 1, wherein the cross feed belt further comprises side rails that are flared outwards.

11. The system of claim 1, further comprising a collection cup sensor that identifies removal and replacement of the collection cup.

12. The system of claim 1, further comprising a lock affixed to a case that contains the medical dispenser.

13. The system of claim 1, further comprising a belt rotation lock that prevents the dispensing belt from rotating when a respective pill module is disengaged from the medical dispenser.

* * * * *